(12) United States Patent
Dong et al.

(10) Patent No.: US 7,873,414 B2
(45) Date of Patent: Jan. 18, 2011

(54) PATIENT CHARACTERISTIC BASED ADAPTIVE ANTI-TACHY PACING PROGRAMMING

(75) Inventors: Yanting Dong, Shoreview, MN (US); Quan Ni, Shoreview, MN (US); Xuan Wei, Plymouth, MN (US); Dan Li, Shoreview, MN (US); Qian Zhong, Los Angeles, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 572 days.

(21) Appl. No.: 11/736,286

(22) Filed: Apr. 17, 2007

(65) Prior Publication Data

US 2008/0262558 A1  Oct. 23, 2008

(51) Int. Cl.
*A61N 1/362* (2006.01)
(52) U.S. Cl. ............................................. 607/14; 607/5
(58) Field of Classification Search ................ 607/1–45, 607/14; 600/643
See application file for complete search history.

(56) References Cited

U.S. PATENT DOCUMENTS

| | | | |
|---|---|---|---|
| 4,114,628 A | 9/1978 | Rizk | |
| 4,773,401 A | 9/1988 | Citak et al. | |
| 4,830,006 A | 5/1989 | Haluska et al. | |
| 5,063,928 A | 11/1991 | Grevis et al. | |
| 5,161,527 A | 11/1992 | Nappholz et al. | |
| 5,163,429 A | 11/1992 | Cohen | |
| 5,183,040 A | 2/1993 | Nappholz et al. | |
| 5,209,229 A | 5/1993 | Gilli | |
| 5,224,475 A | 7/1993 | Berg et al. | |
| 5,251,624 A | 10/1993 | Bocek et al. | |
| 5,330,505 A | 7/1994 | Cohen | |
| 5,342,402 A | 8/1994 | Olson et al. | |

(Continued)

FOREIGN PATENT DOCUMENTS

WO    WO 95/19806 A1   7/1995

(Continued)

OTHER PUBLICATIONS

Brugada, J., et al., "Enhanced Detection Criteria in Implantable Defibrillators.", *J Cardiovasc Electrophysiol.*, 9(3), (Mar. 1998), 261-268.

(Continued)

*Primary Examiner*—Carl H Layno
*Assistant Examiner*—Paula J Stice
(74) *Attorney, Agent, or Firm*—Schwegman, Lundberg & Woessner, P.A.

(57) ABSTRACT

A system including at least one implantable sensor circuit adapted to produce an electrical sensor signal related to one or more physiologic cardiovascular events of a subject, a therapy circuit configured to provide anti-tachycardia pacing (ATP) therapy, and a controller. The controller includes a tachyarrhythmia detection circuit and an efficacy circuit. The tachyarrhythmia detection circuit is configured to detect a tachyarrhythmia episode in the subject using the electrical sensor signal, and to determine whether the tachyarrhythmia episode is of a type that is treatable with ATP. The efficacy circuit is configured to estimate an efficacy of a currently configured ATP therapy for the subject, and the controller is configured to alter a delivery regimen of the currently configured ATP therapy when the estimated ATP therapy efficacy is deemed insufficient. Other systems and methods are described.

37 Claims, 6 Drawing Sheets

U.S. PATENT DOCUMENTS

| | | |
|---|---|---|
| 5,472,453 A | 12/1995 | Alt |
| 5,548,619 A | 8/1996 | Horiike et al. |
| 5,587,970 A | 12/1996 | Greenwood |
| 5,662,688 A | 9/1997 | Haefner et al. |
| 5,683,424 A | 11/1997 | Brown et al. |
| 5,702,427 A | 12/1997 | Ecker et al. |
| 5,788,717 A | 8/1998 | Mann et al. |
| 5,836,971 A | 11/1998 | Starkweather |
| 5,846,263 A | 12/1998 | Peterson et al. |
| 5,855,593 A | 1/1999 | Olson et al. |
| 5,897,575 A | 4/1999 | Wickham |
| 5,978,707 A | 11/1999 | Krig et al. |
| 6,038,476 A | 3/2000 | Schwartz |
| 6,101,414 A | 8/2000 | Kroll |
| 6,128,529 A | 10/2000 | Elser |
| 6,137,308 A | 10/2000 | Nayak |
| 6,151,524 A | 11/2000 | Krig et al. |
| 6,167,308 A | 12/2000 | DeGroot |
| 6,205,357 B1 * | 3/2001 | Ideker et al. .............. 607/14 |
| 6,317,632 B1 | 11/2001 | Krig et al. |
| 6,400,986 B1 | 6/2002 | Sun et al. |
| 6,493,579 B1 | 12/2002 | Gilkerson et al. |
| 6,497,655 B1 | 12/2002 | Linberg et al. |
| 6,522,925 B1 | 2/2003 | Gilkerson et al. |
| 6,584,352 B2 | 6/2003 | Combs et al. |
| 6,636,764 B1 | 10/2003 | Fain et al. |
| 6,648,823 B2 | 11/2003 | Thompson et al. |
| 6,666,826 B2 | 12/2003 | Salo et al. |
| 6,669,631 B2 | 12/2003 | Norris et al. |
| 6,671,547 B2 | 12/2003 | Lyster et al. |
| 6,690,972 B2 | 2/2004 | Colney et al. |
| 6,775,572 B2 | 8/2004 | Zhu et al. |
| 6,801,806 B2 | 10/2004 | Sun et al. |
| 6,838,591 B2 | 1/2005 | Waksmundzki et al. |
| 6,842,644 B2 | 1/2005 | Anderson et al. |
| 6,873,870 B2 | 3/2005 | Ferek-Petric |
| 6,889,081 B2 | 5/2005 | Hsu |
| 7,010,344 B2 | 3/2006 | Burnes et al. |
| 7,010,349 B2 | 3/2006 | Conley et al. |
| 7,027,856 B2 | 4/2006 | Zhou et al. |
| 7,076,298 B2 | 7/2006 | Padmanabhan et al. |
| 7,181,375 B2 | 2/2007 | Rao et al. |
| 7,570,997 B2 * | 8/2009 | Lovett et al. .............. 607/14 |
| 2001/0025137 A1 * | 9/2001 | Webb et al. .............. 600/300 |
| 2002/0026103 A1 | 2/2002 | Norris et al. |
| 2003/0055679 A1 | 3/2003 | Soll et al. |
| 2003/0083703 A1 | 5/2003 | Zhu et al. |
| 2003/0120316 A1 * | 6/2003 | Spinelli et al. .............. 607/14 |
| 2003/0204210 A1 | 10/2003 | Ousdigian et al. |
| 2003/0208241 A1 | 11/2003 | Bradley et al. |
| 2004/0023197 A1 | 2/2004 | Abraham-Fuchs et al. |
| 2004/0103001 A1 | 5/2004 | Mazar et al. |
| 2004/0122294 A1 | 6/2004 | Hatlestad et al. |
| 2004/0152954 A1 | 8/2004 | Pearce et al. |
| 2004/0172068 A1 * | 9/2004 | Sullivan et al. .............. 607/5 |
| 2004/0220624 A1 | 11/2004 | Ritscher et al. |
| 2004/0220634 A1 | 11/2004 | Belk |
| 2004/0230233 A1 * | 11/2004 | Gunderson et al. .............. 607/9 |
| 2005/0070966 A1 | 3/2005 | Sharma |
| 2005/0070967 A1 | 3/2005 | Zhu et al. |
| 2005/0090869 A1 | 4/2005 | Sun et al. |
| 2005/0131477 A1 * | 6/2005 | Meyer et al. .............. 607/27 |
| 2005/0197674 A1 | 9/2005 | McCabe et al. |
| 2005/0245980 A1 | 11/2005 | Belk |
| 2006/0111747 A1 * | 5/2006 | Cazares et al. .............. 607/4 |
| 2006/0149325 A1 | 7/2006 | Zhang |
| 2006/0167506 A1 * | 7/2006 | Stoop et al. .............. 607/9 |
| 2006/0241712 A1 | 10/2006 | Cates et al. |
| 2007/0049974 A1 * | 3/2007 | Li et al. .............. 607/4 |
| 2007/0191896 A1 * | 8/2007 | Belk et al. .............. 607/14 |

FOREIGN PATENT DOCUMENTS

| | | |
|---|---|---|
| WO | WO 98/40122 A1 | 9/1998 |
| WO | WO 2005/107861 A1 | 11/2005 |

OTHER PUBLICATIONS

Brugada, J., "Is Inappropriate Therapy a Resolved Issue With Current Implantable Cardioverter Defibrillators?", *Am J Cardiol.*, 83(5B), (1999), 40D-44D.

Dorian, P., et al., "Randomized Controlled Study of Detection Enhancements Versus Rate-Only Detection to Prevent Inappropriate Therapy in a Dual-Chamber Implantable Cardioverter-Defibrillator", *Heart Rhythm*, 1(5), (2004), 540-547.

Li, D., et al., "Method and Apparatus for Controlling Anti-Tachyarrhythmia Pacing Using Hemodynamic Sensor", U.S. Appl. No. 11/312,082, filed Dec. 20, 2005, 49 Pages.

Li, D., "Method and Apparatus for Morphology-Based Arrhythmia Classification Using Cardiac and Other Physiological Signals", U.S. Appl. No. 11/316,332, filed Dec. 22, 2005, 63 Pages.

Steinbach, K. K., "Hemodynamics During Ventricular Tachyarrhythmias", *American Heart Journal*, 127(4 Pt 2), (1994), 1102-1106.

* cited by examiner

PATIENT CHARACTERISTIC BASED ADAPTIVE ANTI-TACHY PACING PROGRAMMING

FIELD OF THE INVENTION

The field generally relates to implantable medical devices and, in particular, but not by way of limitation, to systems, devices, and methods for providing cardiac arrhythmia therapy to a subject.

BACKGROUND

Implantable medical devices (IMDs) include devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. The devices can be used to treat patients using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability.

Additionally, some IMDs detect events by monitoring electrical heart activity signals. In CFM devices, these events can include heart chamber expansions or contractions. By monitoring cardiac signals indicative of expansions or contractions, IMDs can detect abnormally slow heart rate, or bradycardia. The IMDs can detect abnormally rapid heart rate, or tachyarrhythmia. Ventricular tachyarrhythmia can be terminated with high energy shock therapy using an ICD. However, cardioversion/defibrillation therapy can cause patient discomfort and consumes a relatively large amount of battery power which may lead to a shortened useful device lifetime. Ventricular tachyarrhythmia can be treated with anti-tachycardia pacing (ATP). ATP uses lower energy than cardioversion/defibrillation therapy and may painlessly terminate an episode of ventricular tachyarrhythmia. Therefore it is sometimes desirable to treat ventricular arrhythmias with ATP rather than a shock.

OVERVIEW

This document relates generally to systems, devices, and methods for providing cardiac arrhythmia therapy to a subject. A system example includes at least one implantable sensor circuit adapted to produce an electrical sensor signal related to one or more physiologic cardiovascular events of a subject, a therapy circuit configured to provide anti-tachycardia pacing (ATP) therapy, and a controller. The controller includes a tachyarrhythmia detection circuit and an efficacy circuit. The tachyarrhythmia detection circuit is configured to detect a tachyarrhythmia episode in the subject using the electrical sensor signal, and to determine whether the tachyarrhythmia episode is of a type that is treatable with ATP. The efficacy circuit is configured to estimate an efficacy of a currently configured ATP therapy for the subject, and wherein the controller is configured to alter a delivery regimen of the currently configured ATP therapy when the estimated ATP therapy efficacy is deemed insufficient.

A method example includes detecting a tachyarrhythmia episode in a subject using a medical device, wherein the tachyarrhythmia episode is of a type treatable with anti-tachycardia pacing (ATP), estimating an efficacy of a currently configured ATP therapy for the subject, and altering a delivery regimen of the currently configured ATP therapy when the estimated ATP therapy efficacy is deemed insufficient.

This summary is intended to provide an overview of the present patent application. It is not intended to provide an exclusive or exhaustive explanation of the invention. The detailed description is included to provide further information about the subject matter of the present patent application.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, such that "A or B" includes "A but not B." "B but not A," and "A and B," unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1:
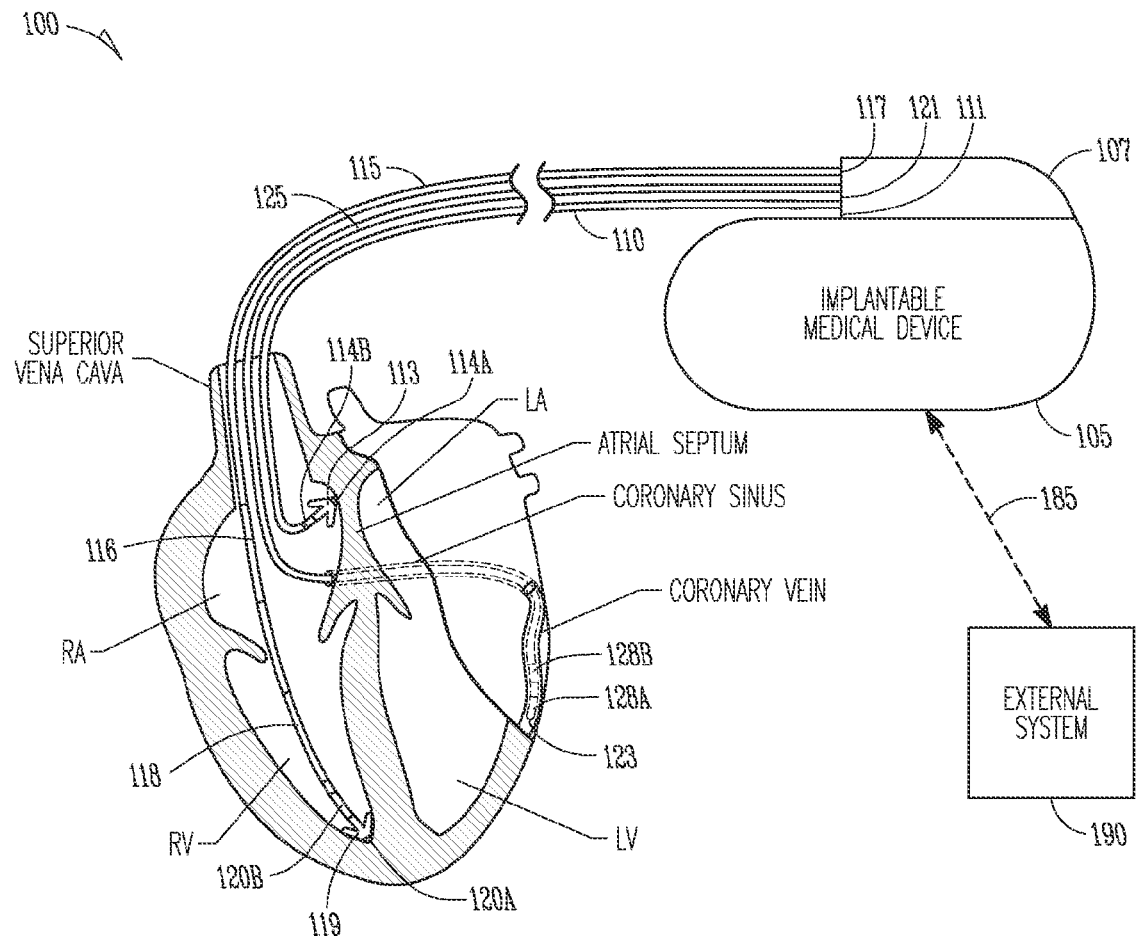
FIG. 1 shows an example of portions of a system that uses an implantable medical device (IMD).

FIG. 1 is an illustration of portions of a system 100 that uses an implantable medical device (IMD) 105. Examples of IMD 105 include, without limitation, a, pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. As one example, the system 100 shown is used to treat a cardiac arrhythmia. The IMD 105 typically includes an electronics unit coupled by one or more cardiac leads 110, 115, 125, to a heart of a patient or subject. The electronics unit of the IMD 105 typically includes components that are enclosed in a hermetically-sealed canister or "can." The system 100 also typically includes an IMD programmer or other external system 190 that communicates one or more wireless signals 185 with the IMD 105, such as by using radio frequency (RF) or one or more other telemetry signals.

The example shown includes right atrial (RA) lead 110 having a proximal end 111 and a distal end 113. The proximal end 111 is coupled to a header connector 107 of the IMD 105. The distal end 113 is configured for placement in the RA in or near the atrial septum. The RA lead 110 may include a pair of bipolar electrodes, such as an RA tip electrode 114A and an RA ring electrode 114B. The RA electrodes 114A and 114B are incorporated into the lead body at distal end 113 for placement in or near the atrial septum, and are each electrically coupled to IMD 105 through a conductor extending within the lead body. The RA lead is shown placed in or near the atrial septum, but the RA lead may be placed in the atrial appendage or elsewhere.

The example shown also includes a right ventricular (RV) lead 115 having a proximal end 117 and a distal end 119. The proximal end 117 is coupled to a header connector 107. The distal end 119 is configured for placement in the RV. The RV lead 115 may include one or more of a proximal defibrillation electrode 116, a distal defibrillation electrode 118, an RV tip electrode 120A, and an RV ring electrode 120B. The defibrillation electrode 116 is generally incorporated into the lead body such as in a location suitable for supraventricular placement in the RA and/or the superior vena cava. The defibrillation electrode 118 is incorporated into the lead body near the distal end 119 such as for placement in the RV. The RV electrodes 120A and 120B may form a bipolar electrode pair and are generally incorporated into the lead body at distal end 119. The electrodes 116, 118, 120A, and 120B are each electrically coupled to IMD 105, such as through one or more conductors extending within the lead body. The proximal defibrillation electrode 116, distal defibrillation electrode 118, or an electrode formed on the can of IMD 105 allow for delivery of cardioversion or defibrillation pulses to the heart.

The RV tip electrode 120A, RV ring electrode 120B, or an electrode formed on the can of IMD 105 allow for sensing an RV electrogram indicative of RV depolarizations and delivering RV pacing pulses. RA tip electrode 114A, RA ring electrode 114B, or an electrode formed on the can of IMD 105 allow for sensing an RA electrogram indicative of RA depolarizations and allow for delivering RA pacing pulses. Sensing and pacing allows the IMD 105 to adjust timing of the heart chamber contractions. In some examples, the IMD 105 can adjust the timing of ventricular contractions with respect to the timing of atrial contractions by sensing a contraction in the RA and pacing the RV at the desired atrial-ventricular (AV) delay time.

A left ventricular (LV) lead 125 can include a coronary pacing or sensing lead that includes an elongate lead body having a proximal end 121 and a distal end 123. The proximal end 121 is coupled to a header connector 107. A distal end 123 is configured for placement or insertion in the coronary vein. The LV lead 125 may include an LV ring or tip electrode 128A and an LV ring electrode 128B. The distal portion of the LV lead 125 is configured for placement in the coronary sinus and coronary vein such that the LV electrodes 128A and 128B are placed in the coronary vein. The LV electrodes 128A and 128B may form a bipolar electrode pair and are typically incorporated into the lead body at distal end 123. Each can be electrically coupled to IMD 105 such as through one or more conductors extending within the lead body. LV tip electrode 128A, LV ring electrode 128B, or an electrode formed on the can of the IMD 105 allow for sensing an LV electrogram indicative of LV depolarizations and delivering LV pacing pulses.

Other forms of electrodes include meshes and patches, which may be applied to one or more portions of heart, or which may be implanted in one or more other areas of the body to help "steer" electrical current produced by the IMD 105 in FIG. 1. The IMDs may be configured with a variety of electrode arrangements or combinations, including transvenous, endocardial, or epicardial electrodes (e.g., intrathoracic electrodes), or subcutaneous, non-intrathoracic electrodes, such as can, header, or indifferent electrodes, or subcutaneous array or lead electrodes (e.g., non-intrathoracic electrodes). Monitoring of one or more electrical signals related to cardiac activity can provide early, if not immediate, diagnosis of cardiac disease.

ATP therapy regimens typically treat fast heart rates through short bursts of rapid pacing into either the atrium or ventricle (depending on where the fast heart rate is detected). Some IMDs can be programmed to provide ATP to any one of the RA, RV, LV, or any combination of the RA, RV, and LV. Additionally, various parameters related to a regimen of ATP therapy are often programmable. Examples of programmable parameters include, among other parameters, the number of bursts in an ATP therapy regimen, the number of pacing pulses in a burst of ATP, the amplitude of the pacing pulses, the pulse width of the pacing pulses, the time between bursts, and the time between pacing pulses in a burst. Other parameters may include a coupling interval and a timeout time duration. The coupling interval can represent the time between an abnormal rhythm depolarization and the first ATP pulse. For capture of the heart to be achieved and normal sinus rhythm (NSR) restores, it is preferable for the end of the coupling interval to occur when the ventricle is non-refractory. When a timeout for the ATP therapy occurs without capture, the CFM device may change over to delivering high-energy shock therapy.

Figure 2:
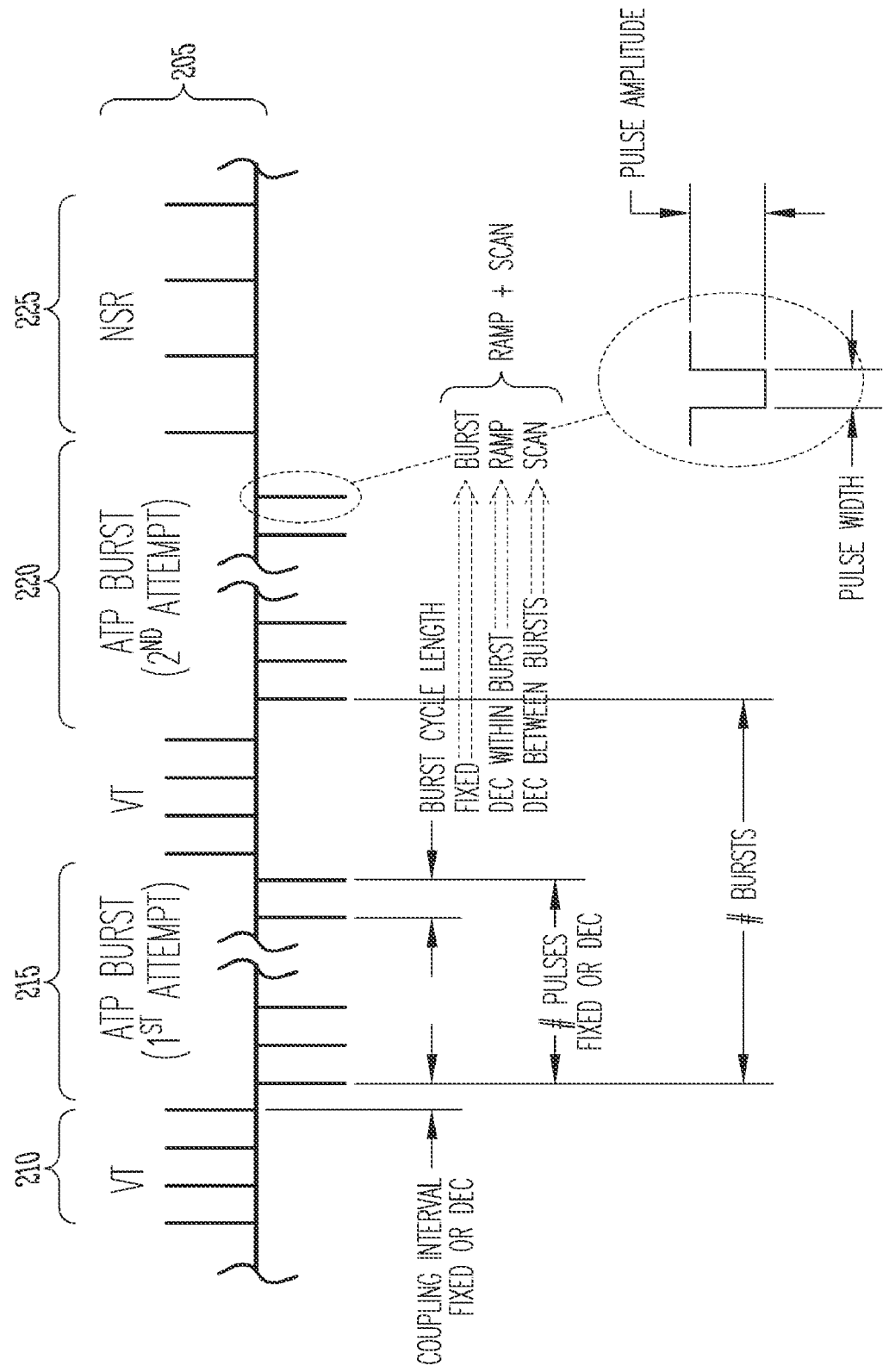
FIG. 2 illustrates an example of ATP therapy.

FIG. 2 illustrates an example of ATP therapy. In this example, a pulse train 205 shows a first set of VT pulses 210 that are intrinsic cardiac depolarizations due to ventricular tachyarrhythmia. The first set of VT pulses 210 are followed by a first attempt of ATP therapy 215 which includes one burst of at least five pulses. The number of pulses in each burst may be fixed or the number of pulses in each burst can be decremented or incremented from one burst to the next. The example also shows the coupling interval which can also be fixed or can be decremented from one attempt of ATP therapy to the next. The time between pulses in a burst, sometimes referred to as a burst cycle length can be fixed (e.g., Burst mode), or decremented within the burst (e.g., Ramp mode) or decremented between bursts (e.g., Scan mode). A combination of Ramp and Scan mode is also possible. The example shows that after the second attempt of ATP therapy 220, the rhythm returns to NSR 225.

This illustrated flexibility in delivering ATP therapy is useful in designing a device that can programmed to provide multiple ATP regimens. Which ATP regimen is most appropriate for a particular patient or subject may depend on the patient's particular physiologic condition as well the history of ATP efficacy for that particular patient and for patients with that particular physiologic condition. It is sometimes desirable to have a system that automatically adapts the ATP therapy according to the patient physiologic condition and the history of ATP therapy efficacy.

Figure 3:
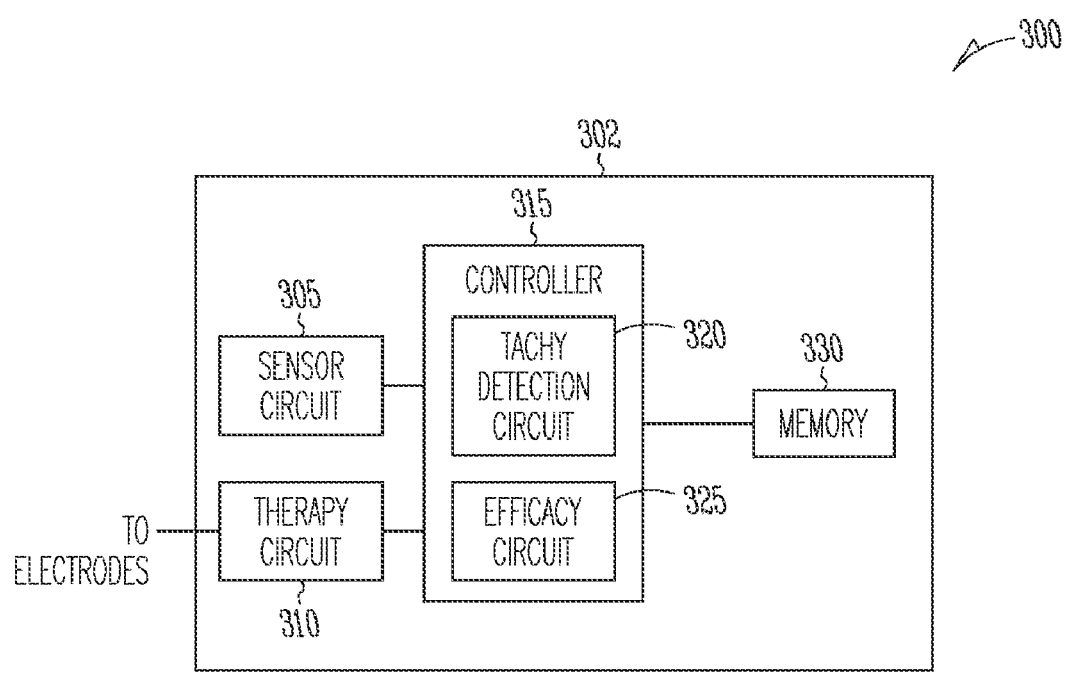
FIG. 3 is block diagram of an example of portions of a system to provide adaptive ATP therapy.

FIG. 3 is block diagram of an example of portions of a system 300 including device 302 to provide adaptive ATP therapy. In this example, the device 302 includes at least one implantable sensor circuit 305, a therapy circuit 310 to provide ATP therapy, and a controller 315. The sensor circuit 305 produces an electrical sensor signal related to one or more physiologic events of a subject.

In some examples, the sensor circuit 305 includes an implantable cardiac signal sensing circuit to sense intrinsic cardiac signals of the subject. Intrinsic cardiac signals such as electrocardiogram (ECG) signals originate from electrophysiological signals originating in and propagated through the cardiac tissue, which provide for the cardiac muscle contraction that pumps blood through the body. Examples of cardiac signal sensing circuits include subcutaneous ECG circuits, intracardiac electrogram (EGM) sensing circuits, and wireless ECG circuits. In a subcutaneous ECG sensing circuit, electrodes are implanted just beneath the skin and the ECG signal obtained is referred to as subcutaneous ECG or far-field electrogram. In an intracardiac EGM circuit and in a wireless ECG circuit, at least one electrode is placed in or around the heart as is described above. A wireless ECG includes a plurality of electrodes to provide differential sensing of cardiac signals to approximate a surface ECG. Descriptions of wireless ECG systems are found in commonly assigned, co-pending U.S. Patent Application Publication No. 2005/0197674 by McCabe et al., entitled "Wireless ECG in Implantable Devices," filed on Mar. 5, 2004, which is incorporated herein by reference.

In some examples, the sensor circuit 305 includes a sensor that produces an electrical signal representative of some aspect of patient hemodynamics. In certain examples, the sensor circuit 305 includes an implantable cardiac blood pressure sensor to measure chamber pressure. In an example, a pressure sensor is implanted in a coronary vessel to determine left ventricle pressure by direct measurement of coronary vessel pressure. Because the pressure sensor varies its output with changes in pressure as occur during heart chamber expansions and contractions, the pressure can provide a signal indicative of activity of the heart. A description of systems and methods that use such an implantable pressure sensor is found in Salo et al., U.S. Pat. No. 6,666,826, entitled "Method and Apparatus for Measuring Left Ventricular Pressure," filed Jan. 4, 2002, which is incorporated herein by reference. Other cardiac pressure sensors examples include a right ventricle (RV) chamber pressure sensor, a pulmonary artery pressure sensor, and a left atrial chamber pressure sensor.

In certain examples, the sensor circuit 305 includes an intracardiac impedance sensor. Electrodes placed within a chamber of the heart provide a signal of impedance versus time. Intracardiac impedance will vary with the filling and emptying of blood in the chamber. This variation creates an intracardiac impedance waveform that can be signal processed to obtain a signal indicative of activity of the heart. Systems and methods to measure intracardiac impedance are described in Citak et al., U.S. Pat. No. 4,773,401, entitled "Physiologic Control of Pacemaker Rate Using Pre-Ejection Interval as the Controlling Parameter," filed Aug. 21, 1987, which is incorporated herein by reference.

The controller 315 circuit may include a digital signal processor, application specific integrated circuit (ASIC), microprocessor, or other type of processor, interpreting or executing instructions in software or firmware. In some examples, the controller 315 may include a state machine or sequencer that is implemented in hardware circuits. The controller 315 may include any combination of hardware, firmware, or software. The controller 315 includes one or more circuits to perform the functions described herein. A circuit may include software, hardware, firmware or any combination thereof. For example, the circuit may include instructions in software executing on the controller 315. Multiple functions may be performed by one or more circuits.

The controller 315 includes a tachyarrhythmia detection circuit 320. The tachyarrhythmia detection circuit 320 detects a tachyarrhythmia episode in the subject using the electrical sensor signal from the sensor circuit 305, and determines whether the tachyarrhythmia episode is of a type that is treatable with ATP. In some examples, the tachyarrhythmia detection circuit 320 detects a tachyarrhythmia episode using heart rate. CFMs that detect tachyarrhythmia may divide the spectrum of possible heart rates into zones. For example, if a CFM detects that a heart rate falls within a zone that defines ventricular tachycardia, the ICD may then trigger other detection methods to confirm that a patient is indeed experiencing ventricular tachycardia.

In some examples, the tachyarrhythmia detection circuit 320 detects a tachyarrhythmia episode by comparing the morphology of a sensed cardiac signal to a morphology template stored in a memory. In some examples, the morphology of a sensed cardiac depolarization is compared to a template of a known normal or abnormal depolarization morphology (such as normal sinus rhythm, ventricular tachyarrhythmia, or supra-ventricular tachyarrhythmia) stored in memory. For example, a template can be created for a patient using a CRM by providing electrical energy pulses to the supra-ventricular region of the patient's heart. The resulting cardiac complexes are then sensed and used to create a template for use in a morphology-based cardiac signal classification algorithm. Systems and methods of creating templates for a morphology-based algorithm are described in Hsu, U.S. Pat. No. 6,889,081, entitled "Classification of Supra-ventricular and Ventricular Cardiac Rhythms Using Cross Channel Timing Algorithm," filed Jul. 23, 2002, which is incorporated herein by reference.

The controller 315 also includes an efficacy circuit 325 configured to estimate an efficacy of a currently configured ATP therapy for the subject. The controller 315 is configured to alter a delivery regimen of the currently configured ATP therapy when the estimated ATP therapy efficacy is deemed insufficient. According to some examples, the controller 315 is configured to perform retrospective analysis to determine if the ATP therapy efficacy is insufficient.

In retrospective analysis, the chance of success of the next application of the currently configured ATP therapy regimen is determined using the arrhythmia conversion history of a previous number of applications. For example, for patients with LVEF$\leq$30%, if the last application of a certain ATP therapy failed to convert the rhythm, the chance of success of the next application of the same therapy will be about 60%, or conversely, the chance that the next application will fail is about 40%. For patients with LVEF>30%, if the last application of ATP therapy failed to convert the rhythm, the chance that the next application will succeed is about 90%, or conversely, the chance that the next application will fail is about 10%. Thus, for patients with the physiologic condition of LVEF$\leq$30%, a previous ATP therapy failure suggests a higher likelihood of further ATP therapy failure.

In certain examples, the device 302 includes a memory 330 communicatively coupled to the controller. The memory 330 stores at least one conversion indication for the currently configured ATP therapy for multiple previous tachyarrhythmia episodes of the subject. The efficacy circuit 325 estimates the efficacy of the currently configured ATP therapy using a conversion rate of the multiple previous tachyarrhythmia episodes.

For example, the controller 315 may store an indication in memory 330 to show a success of administering ATP therapy.

A register or a location of a memory may hold an indication that X out of Y ATP therapy applications were successful (or alternatively, X out of Y were failures), or the indication may be a percentage of success. For example, the controller 315 may deem that the ATP therapy was insufficient if the ATP therapy failed in any of the last predetermined number Y of previous tachyarrhythmia episodes. In another example, the controller 315 may deem that the ATP therapy was insufficient if the therapy was only successful in one out of the last five previous episodes, or 20% successful. In some examples, the memory 330 stores multiple ATP regimens. The controller 315 may store an indication of success (or alternatively of failure) for each available regimen.

In some examples, the number of previous tachyarrhythmia episodes in which to check for a successful rhythm conversion is specified according to a physiologic condition of the subject. For example, the physiologic condition of the patient may be related to left ventricle ejection fraction (LVEF) of the patient. In an illustrative example, if the LVEF of the patient is greater than 30%, the controller 315 may look whether there is a success or a minimum number of successes in the five previous tachyarrhythmia episodes. If the LVEF of the patient is less than 30%, the controller 315 may look whether there is a success in the last two previous tachyarrhythmia episodes. In some examples, the memory 330 stores multiple ATP therapy regimens. One or more ATP therapy regimens may be correlated to a physiologic condition of the subject. The controller 315 may store an indication of success for each ATP therapy regimen available for the physical condition of the subject.

Other physiologic conditions may be used to specify a number of previous tachyarrhythmia episodes for estimating the efficacy of ATP therapy. A non-exhaustive list of such physiologic conditions includes the gender of the patient, whether the age of the patient is higher than a threshold age (e.g., 65), whether the patient is a smoker, whether the patient is being treated for high blood pressure, whether the body mass index (BMI) of the patient is greater than a threshold BMI (e.g., BMI>28), whether the patient is of a certain ethnicity, whether the patient exercises more than a threshold number of hours each week, whether the patient has coronary artery disease, whether the patient has a coronary artery bypass graft, whether the patient has been prescribed beta blockers, the NYHA classification of the patient, whether the patient has bundle branch block, whether the patient has developed ischemic tissue in the past, whether the patient has experienced syncope, the degree of atrial-ventricular (A-V) block of the patient, the degree of sinus node dysfunction of the patient, whether the patient has a stent, whether the patient has a CFM device that paces both ventricular chambers, whether the tachyarrhythmia episode includes atrial fibrillation, and whether the tachyarrhythmia episode includes ventricular tachycardia.

Figure 4:
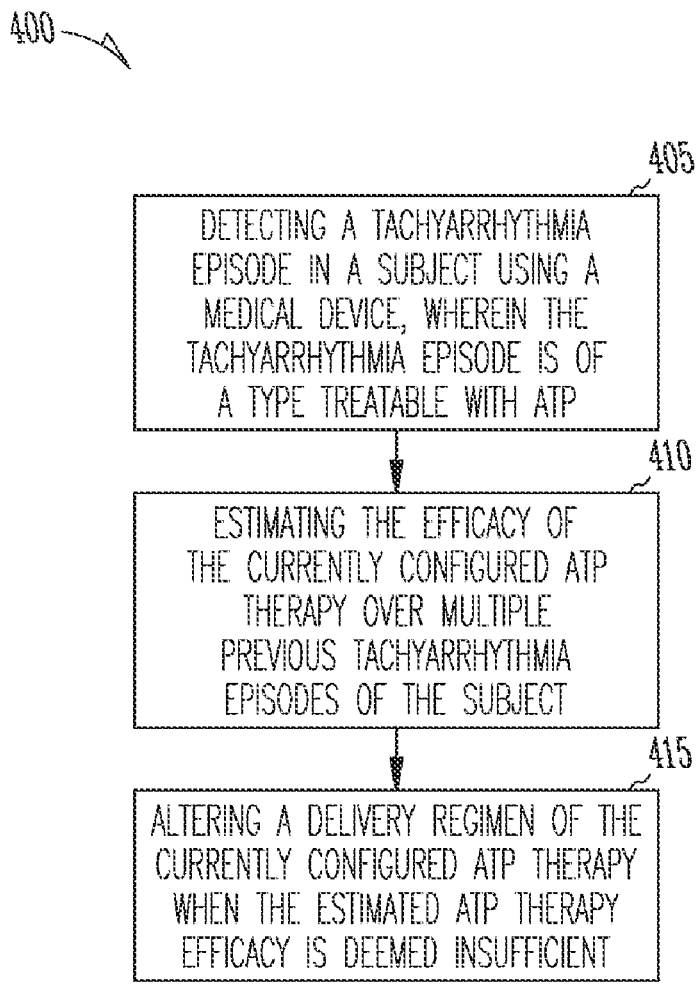
FIG. 4 is a diagram of an example of a method to provide adaptive ATP therapy.

FIG. 4 is a diagram of an example of a method 400 of to provide adaptive ATP therapy. At 405, a tachyarrhythmia episode is detected in a subject using a medical device. The tachyarrhythmia episode is of a type treatable with anti-tachycardia pacing (ATP). At 410, an efficacy of a currently configured ATP therapy is estimated for the subject. In some examples, the efficacy is determined over a specified number of previous tachyarrhythmia episodes. In certain examples, the number of previous tachyarrhythmia episodes is determined from a physiologic condition of the subject. At 415, a delivery regimen of the currently configured ATP therapy is altered when the estimated ATP therapy efficacy is deemed insufficient.

In some examples, the efficacy circuit 325 of FIG. 3 is configured for determining a cumulative subject-specific efficacy of the currently configured ATP therapy. The efficacy circuit 325 may determine the efficacy from the number of ATP successes within a predetermined time period (or alternatively, from the failures). In some examples, the efficacy is calculated as a percentage of applied ATP therapy regimens that were ultimately successful in converting the arrhythmia to a normal rhythm. The controller 315 compares the cumulative subject-specific efficacy to a physiologic condition-specific efficacy threshold. The controller 315 alters the delivery regimen of the ATP therapy when the cumulative subject-specific efficacy is less than the physiologic condition-specific efficacy threshold. To make the comparison, the physiologic condition-specific efficacy threshold may be communicated to the device 302 from a second separate device.

Figure 5:
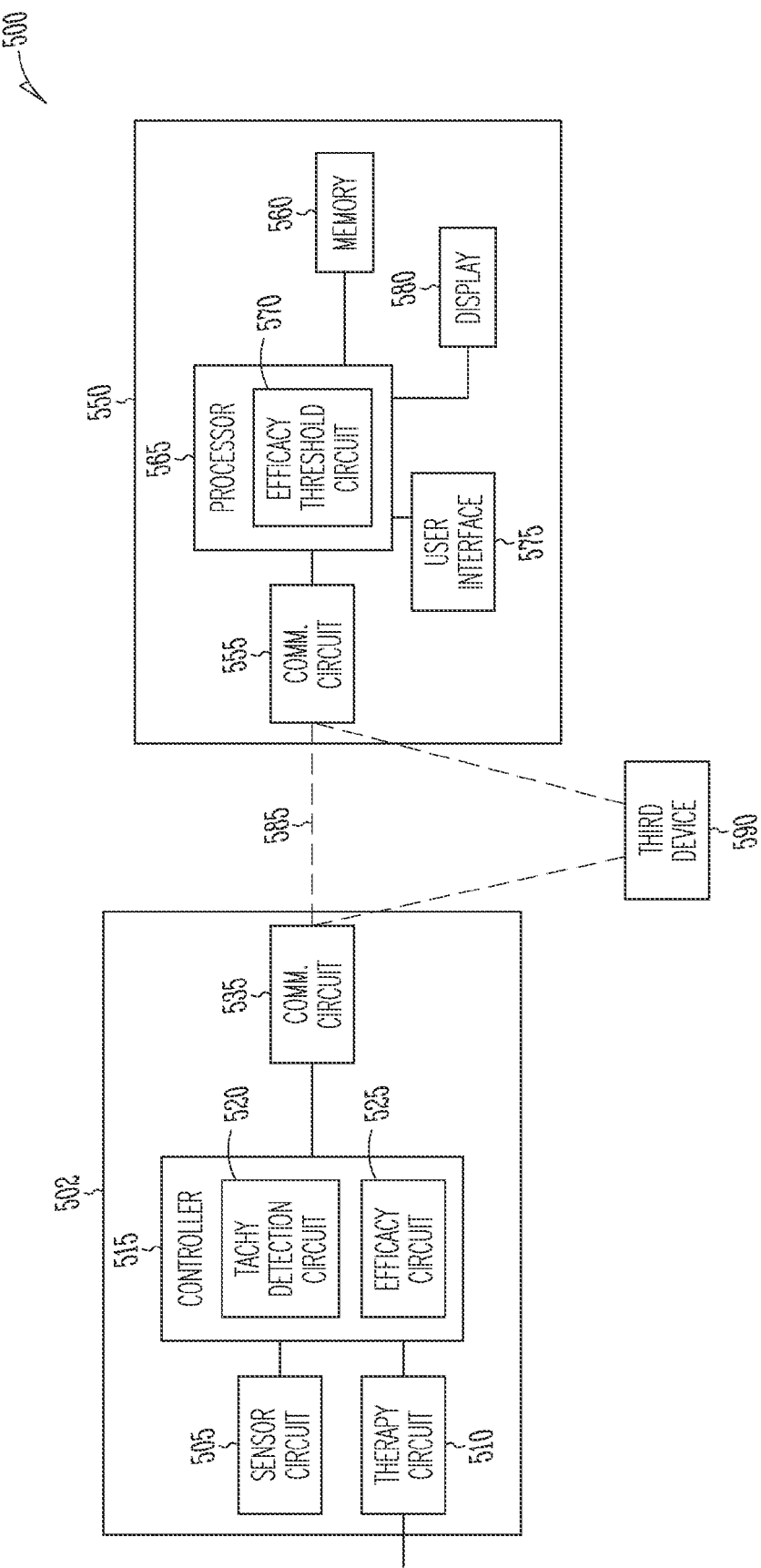
FIG. 5 is block diagram of an example of portions of a system to provide adaptive ATP therapy.

FIG. 5 is block diagram of an example of portions of a system 500 to provide adaptive ATP therapy. The system 500 includes a first device 502 and a second device 550. The first device 502 includes at least one implantable sensor circuit 505, a therapy circuit 510 to provide ATP therapy, and a controller 515. The controller 515 includes a tachyarrhythmia detection circuit 520 and an efficacy circuit 525. In some examples, the first device 502 is an IMD.

The second device 550 includes a communication circuit 555 configured to communicate one or more wireless signals 585 with the first device 502. The second device 550 also includes a memory 560 to store data related to conversion of tachyarrhythmia by ATP therapy and a processor 565 communicatively coupled to the communication circuit 555 and memory 560.

The processor 565 includes an efficacy threshold circuit 570. The efficacy threshold circuit 570 is configured for receiving an indication of a physiologic condition of the subject and the currently configured ATP therapy of the first device, checking the memory 560 for data related to conversion of tachyarrhythmia by ATP therapy for that physiologic condition and determining the physiologic condition-specific efficacy threshold. The processor 565 may then communicate the physiologic condition-specific efficacy to the first device 502 using the communication circuit 555. The controller 515 compares a calculated cumulative subject-specific efficacy to the communicated physiologic condition-specific efficacy threshold. The controller 515 alters a delivery regimen of ATP therapy when the cumulative subject-specific efficacy is less than the physiologic condition-specific efficacy threshold.

In some examples, the second device 550 includes a medical device programmer. In some examples, the second device 550 includes a server for storing data. The server may be communicatively coupled to a communication network, such as the internet or a cell phone network. In certain examples, the second device 550 is remote from the first device 502 and the second device 550 communicates with the first device 502 using a third device 590, such as a repeater placed in proximity to the patient for example, which communicates with both devices.

In some examples, the memory 560 includes a database including data from several patient populations. To determine the physiologic condition-specific efficacy threshold, the second device 550 checks the memory 560 for data related to conversions of tachyarrhythmia by ATP therapy for that physiologic condition. The efficacy threshold circuit 570 determines the expected ATP efficacy for the patient population having the physiologic condition and being treated with a particular ATP therapy.

The second device 550 may recurrently search the database for data related to the physiologic condition and conversion of tachyarrhythmia by ATP therapy (e.g., periodically such every certain of days, or when new data related to tachyarrhythmia episodes is made available to the data base). This can be viewed as mining the database for the data. In some examples, second device 550 may search the database for the data in response to a communication with the first device 502. For instance, the second device 550 may receive an indication that a patient experienced a tachyarrhythmia episode either manually entered into the second device 550 or received from the first device 502. The efficacy threshold circuit 570 may use a statistical model to determine the physiologic condition-specific efficacy threshold. The statistical model may be a parametric or a non-parametric model. The determination of the efficacy may be initiated by a search of the database.

As an illustrative example, assume the patient condition is the degree of LVEF of the patient; specifically, whether the LVEF of the patient is above 30%. The efficacy threshold circuit 570 determines from the database that the physiologic condition-specific efficacy threshold for patients having LVEF>30% is 90% while the physiologic condition-specific efficacy threshold for patients having LVEF≦30% is 83%. These thresholds may be determined from a significant population of patients with LVEF contained in the database. If a subject has LVEF>30% and the subject-specific cumulative efficacy determined by the first device 502 indicates the subject is experiencing a conversion rate of 90% or higher, then the current ATP therapy continues to be delivered according to the current regimen. If the subject-specific cumulative efficacy determined by the first device 502 indicates the subject is experiencing a conversion rate less than 90% or less than 90% by a specified percentage, then the ATP therapy can be switched to a different ATP therapy regimen.

Figure 6:
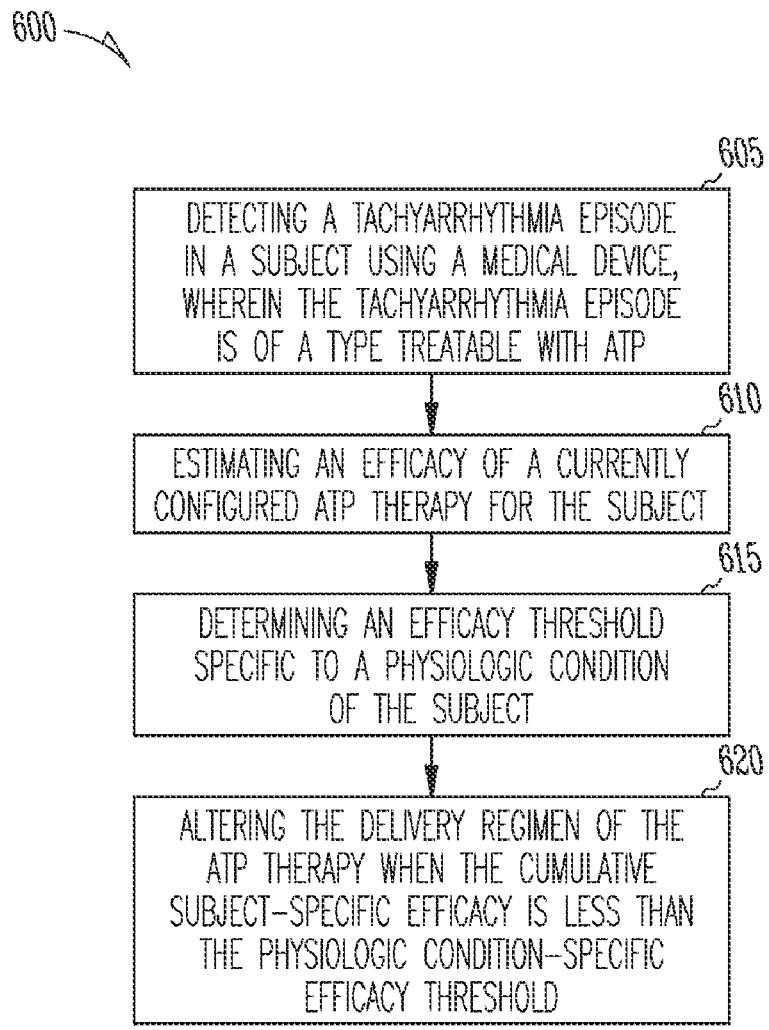
FIG. 6 is a diagram of an example of a method to provide adaptive ATP therapy.

FIG. 6 is a diagram of an example of a method 600 of to provide adaptive ATP therapy. At 605, a tachyarrhythmia episode is detected in a subject using a medical device. The tachyarrhythmia episode is of a type treatable with anti-tachycardia pacing (ATP). At 610, an efficacy of a currently configured ATP therapy is estimated for the subject. In some examples, estimating the efficacy includes determining a cumulative subject-specific efficacy of the currently configured ATP therapy. At 615, an efficacy threshold specific to a physiologic condition of the subject is determined. At 620, a delivery regimen of the currently configured ATP therapy is altered when the estimated ATP therapy efficacy is deemed insufficient because the cumulative subject-specific efficacy is less than the physiologic condition-specific efficacy threshold.

The second device 550 may store or track more than one physiologic condition-specific efficacy threshold. To know which physiologic condition-specific efficacy threshold to communicate to the first device 502, in some examples the efficacy threshold circuit 570 is configured to receive the indication of a physiologic condition of the subject via the communication circuit 555. The first device 502 may include a memory to store an indication of the physiologic condition of the subject and a communication circuit 535 configured to communicate information about the indication of the physiologic condition and the physiologic condition-specific efficacy threshold with the second device 550.

In some examples, the second device 550 includes a user interface 575 operatively coupled to the processor 565. The efficacy threshold circuit 570 is configured to receive the indication of a physiologic condition of the subject manually entered via the user interface 575. The user interface 575 may include a keyboard or keypad and/or a computer mouse. The second device 550 then communicates the appropriate physiologic condition-specific efficacy threshold to the first device 502. In some examples, the second device 550 includes a display 580 operatively coupled to the processor 565. The processor 565 may display a determined physiologic condition-specific efficacy threshold. In some examples, the processor 565 displays at least a portion of the data used to determine the physiologic condition-specific efficacy threshold. This is useful to present results if data mining is initiated by a user to determine a physiologic condition-specific efficacy threshold.

In some examples, the second device 550 communicates the physiologic condition-specific efficacy threshold to the first device 502. The first device 502 compares the subject-specific efficacy to the physiologic condition-specific efficacy threshold to determine whether the efficacy of the currently configured ATP therapy is insufficient. The result of the comparison, or an indication of efficacy, is communicated to the second device 550 which displays whether the efficacy is sufficient or insufficient.

In some examples, the second device 550 receives an indication of the physiologic condition of the subject and the currently configured ATP therapy of the first device 502 via the communication circuit 555. The second device includes an indicator circuit to provide an indication that an estimated efficacy of the currently configured ATP therapy for the subject is deemed insufficient. In certain examples, the indicator circuit is a display.

In some examples, the first device 502 communicates the physiologic condition and subject-specific efficacy of the currently configured ATP therapy to the second device 550. The second device 550 compares the subject-specific efficacy to the physiologic condition-specific efficacy threshold. The physiologic condition-specific efficacy threshold may be a previously stored threshold or may be determined from a calculation initiated by a user. The second device 550 includes an indicator circuit, such as a display 580, to provide an indication that the efficacy of the currently configured ATP therapy is insufficient. The second device 550 then displays a recommended change to the currently configured ATP therapy. The second device 550 may store a plurality of ATP therapy regimens in memory 560 and the processor 565 may display an alternate ATP therapy. The second device 550 may initiate a change to the currently configured ATP therapy after an indication of confirmation is received into the second device 550, such as through the user interface 575 for example. The second device initiates the change by downloading the confirmed ATP regimen to the first device 502.

As described above, the controller 515 alters a delivery regimen of ATP therapy when the ATP therapy efficacy is deemed insufficient, such as when a cumulative subject-specific efficacy is less than a physiologic condition-specific efficacy threshold. In some examples, the first device 502 includes a memory to store at least one parameter related to the currently configured ATP therapy. The controller 515 alters the ATP therapy delivery regimen by changing the stored parameter to a new value when the ATP therapy efficacy is deemed insufficient. In some examples, the first device 502 has the new value and the controller 515 writes the new value into a memory location. In some examples, the first device 502 receives the new value for the parameter from the second device 550 and the controller 515 writes the received value into memory.

In some examples, the first device 502 stores a plurality of ATP therapy regimens in the memory. To alter the delivery regimen the controller 515 changes from the currently configured ATP therapy to a different ATP therapy regimen stored in the medical device when the ATP therapy efficacy is deemed insufficient. For example, a specific ATP therapy regimen may be designated as a set of parameters placed in one area of memory. Changing to a new regimen may involve moving the parameters into a second area of memory reserved for the operating parameters of the currently operating ATP therapy.

In some examples, a plurality of ATP therapy regimens may be stored in memory of the first device 502. The regimens may be prioritized according to an order of use. The controller 515 may be configured to first try the regimen with the highest priority and then move through the prioritized regimens if the arrhythmia is not converted by regimens of higher priority. In some examples, the controller 515 re-prioritizes the plurality of ATP therapy regimens when the ATP therapy efficacy is deemed insufficient (e.g., the controller 515 may attempt the plurality of regimens in a different order).

In some examples, the tachyarrhythmia detection circuit 520 may divide the spectrum of possible heart rates into zones. If the tachyarrhythmia detection circuit 520 detects that a heart rate falls within a specified rate zone that defines a type of tachyarrhythmia such as ventricular tachycardia, the first device 502 may then trigger other detection methods to confirm the type of tachyarrhythmia. In some examples, the first device 502 stores at least one ATP therapy regimen in accordance with a tachyarrhythmia rate zone. In some examples, the controller 515 alters an ATP therapy regimen specified for that tachyarrhythmia rate zone when the estimated ATP therapy efficacy is deemed insufficient.

It is to be understood that the above description is intended to be illustrative, and not restrictive. For example, the above-described embodiments (and/or aspects thereof) may be used in combination with each other. As another example, although the above description has emphasized the use of a PA pressure sensor, in other examples, other blood pressure sensors or signals can be used in conjunction with the various techniques or apparatuses described herein. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A system comprising:
a first device including:
at least one implantable sensor circuit configured to produce an electrical sensor signal related to one or more physiologic cardiovascular events of a subject;
a therapy circuit configured to provide anti-tachycardia pacing (ATP) therapy and
a controller, communicatively coupled to the sensor circuit and the therapy circuit, the controller including:
a tachyarrhythmia detection circuit configured to detect a tachyarrhythmia episode in the subject using the electrical sensor signal, and to determine whether the tachyarrhythmia episode is of a type that is treatable with ATP; and
an efficacy circuit configured to, before beginning delivery of a currently configured ATP therapy in response to the detected tachyarrhythmia episode, estimate a cumulative subject-specific currently-configured ATP therapy efficacy, and wherein the controller is configured to: compare the cumulative subject-specific efficacy to a physiological condition specific efficacy threshold determined using a patient population; and alter the delivery regimen of the ATP therapy when the cumulative subject-specific efficacy is less than the physiological condition-specific efficacy threshold.

2. The system of claim 1, comprising a second device including:
a communication circuit;
a memory configured to store data related to conversion of tachyarrhythmia by ATP therapy; and
a processor, communicatively coupled to the communication circuit and the memory, including an efficacy threshold circuit configured to:
receive an indication of a physiologic condition of the subject and the currently configured ATP therapy of the first device;
check the memory for data related to conversion of tachyarrhythmia by ATP therapy for the physiologic condition; and
determine the physiologic condition-specific efficacy threshold, and wherein the processor is configured to communicate the physiologic condition-specific efficacy using the communication circuit.

3. The system of claim 2, wherein the efficacy threshold circuit is configured to receive the indication of a physiologic condition of the subject via the communication circuit.

4. The system of claim 2, wherein the second device includes a user interface configured to be coupled to the processor, and wherein the efficacy threshold circuit is configured to receive the indication of a physiologic condition of the subject via the user interface.

5. The system of claim 2, wherein the second device includes a server communicatively coupled to a communication network.

6. The system of claim 5, wherein the first device includes:
a memory configured to store an indication of the physiologic condition of the subject; and
a communication circuit configured to communicate to a separate device information about the indication of the physiologic condition and the physiologic condition-specific efficacy threshold.

7. The system of claim 5, including a third device configured to communicate information between the first device and the second device.

8. The system of claim 2, wherein the second device includes a display configured to be coupled to the processor, and wherein the processor is configured to display at least one of an efficacy estimated using at least a portion of the data.

9. The system of claim 8, wherein the processor is configured to display an indication of an alternate ATP therapy and to initiate a change to the currently configured ATP therapy after an indication of a confirmation is received by the second device, wherein the second device is separate from the first device.

10. The system of claim 1, wherein the first device comprises:
a memory, communicatively coupled to the controller, to store an indication of tachyarrhythmia conversion for the currently configured ATP therapy for multiple previous tachyarrhythmia episodes of the subject; and
wherein the efficacy circuit is configured to estimate the cumulative subject-specific currently-configured ATP therapy efficacy using conversion success information about the multiple previous.

11. The system of claim 10, wherein the memory is configured to store the indication of tachyarrhythmia conversion for a number of previous tachyarrhythmia episodes, wherein the number of previous tachyarrhythmia episodes is specified according to a physiologic condition of the subject.

12. The system of claim 1, wherein the first device includes a memory, communicatively coupled to the controller, configured to store at least one parameter related to the currently configured ATP therapy, and wherein the controller is configured to change the parameter when the cumulative subject-specific currently-configured ATP therapy efficacy is deemed insufficient.

13. The system of claim 12, wherein the first device includes a communication circuit, communicatively coupled to the controller, configured to receive the parameter from a separate device.

14. The system of claim 1, wherein the first device includes a memory, communicatively coupled to the controller, configured to store a plurality of ATP therapy regimens, and wherein the controller is configured to change from the currently configured ATP therapy to a different ATP therapy regimen stored in the medical device when the cumulative subject-specific currently-configured ATP therapy efficacy is deemed insufficient.

15. The system of claim 1, wherein the first device includes a memory, communicatively coupled to the controller, configured to store a plurality of ATP therapy regimens, and wherein the controller is configured to re-prioritize the ATP therapy regimens when the cumulative subject-specific currently-configured ATP therapy efficacy is deemed insufficient.

16. The system of claim 1, wherein the controller is configured to cancel the currently configured ATP therapy when the estimated cumulative subject-specific currently-configured ATP therapy efficacy is deemed insufficient.

17. The system of claim 1, wherein the therapy circuit is configured to deliver high-energy shock therapy, and wherein the controller is configured to initiate high-energy shock therapy when the cumulative subject-specific currently-configured ATP therapy efficacy is deemed insufficient.

18. The system of claim 1, including:
a memory, coupled to the controller, configured to store at least one ATP therapy in correspondence with a tachyarrhythmia rate zone;
wherein the tachyarrhythmia detection circuit is configured to detect the tachyarrhythmia episode when a heart rate of the subject is within a specified tachyarrhythmia rate zone; and
wherein the controller is configured to alter, when the cumulative subject-specific currently-configured ATP therapy efficacy is deemed insufficient, a delivery regimen including altering an ATP therapy regimen corresponding to a tachyarrhythmia rate zone corresponding to the heart rate of the tachyarrhythmia.

19. The system of claim 1, comprising a second device including:
a communication circuit configured to receive an indication of a physiologic condition of the subject and the currently configured ATP therapy of the first device; and
an indicator circuit configured to provide an indication that an estimated currently configured ATP therapy efficacy for the subject is deemed insufficient.

20. The system of claim 19, wherein the indicator circuit includes a display to display the indication and to display a recommended change to the currently configured ATP therapy.

21. A method comprising:
detecting a tachyarrhythmia episode in a subject using a medical device, wherein the tachyarrhythmia episode is of a type treatable with anti-tachycardia pacing (ATP);
before beginning delivery of the currently configured ATP therapy in response to the detected tachyarrhythmia episode, estimating an efficacy for the subject of an ATP therapy currently configured in the medical device;
comparing the estimated efficacy to a physiological condition-specific threshold value, wherein the efficacy threshold value is statistically determined using a patient population; and
altering a delivery regimen of the currently configured ATP therapy when the estimated efficacy of the ATP therapy is deemed insufficient.

22. The method of claim 21, including:
determining a physiologic condition-specific efficacy threshold that is specific to a physiologic condition of the subject;
determining a cumulative subject-specific currently configured ATP therapy efficacy, wherein comparing the estimated efficacy to a specified efficacy threshold value includes comparing the cumulative subject-specific ATP therapy efficacy to the physiologic condition-specific efficacy threshold; and
altering the delivery regimen of the ATP therapy when the cumulative subject-specific ATP therapy efficacy is less than the physiologic condition-specific efficacy threshold.

23. The method of claim 22, wherein determining the physiologic condition-specific efficacy threshold includes:
recurrently checking for stored data related to efficacy of ATP therapy;
using at least some of the data to estimate a physiologic condition-specific currently configured ATP therapy efficacy; and
communicating information about the physiologic condition-specific currently configured ATP therapy efficacy.

24. The method of claim 23, including displaying at least one of an efficacy determined using at least some of the data and at least a portion of the data.

25. The method of claim 21, wherein the estimating the efficacy includes estimating the currently configured ATP therapy efficacy over multiple previous tachyarrhythmia episodes of the subject.

26. The method of claim 25, including using the physiologic condition of the subject for determining a specified number of previous tachyarrhythmia episodes for the estimating the efficacy.

27. The method of claim 21, wherein the altering the delivery regimen includes changing the currently configured ATP therapy.

28. The method of claim 27, wherein changing the currently configured ATP therapy includes downloading a different ATP therapy regimen from a remote external device to the medical device.

29. The method of claim 27, wherein changing the currently configured ATP therapy includes downloading a different ATP therapy regimen from a local external device to the medical device.

30. The method of claim 27, wherein changing the currently configured ATP therapy includes changing to a different ATP therapy regimen stored in the medical device.

31. The method of claim 27, wherein changing the currently configured ATP therapy includes re-prioritizing ATP regimens stored in the medical device.

32. The method of claim 27, wherein the changing the currently configured ATP therapy includes displaying an alternate ATP therapy on a separate second device and changing the currently configured ATP therapy after an indication of confirmation is received into the separate second device.

33. The method of claim 21, wherein the altering the therapy regimen includes canceling the currently configured ATP therapy.

34. The method of claim 21, including detecting a heart rate that is within a specified tachyarrhythmia rate zone, and wherein the altering a delivery regimen includes altering a delivery regimen of the currently configured ATP therapy corresponding to the specified tachyarrhythmia rate zone.

35. The method of claim 21, wherein the altering the therapy regimen includes generating an indication that an efficacy of the currently configured ATP therapy for the subject is less than a specified efficacy threshold.

36. The method of claim 35, including displaying a recommended change to the currently configured ATP therapy.

37. A system comprising:
   means for detecting a tachyarrhythmia episode in a subject using a medical device, wherein the tachyarrhythmia episode is of a type treatable with anti-tachycardia pacing (ATP);
   means for, before beginning delivery of the currently configured ATP therapy in response to the detected tachyarrhythmia episode, estimating an efficacy for the subject of an ATP therapy currently configured in the medical device;
   means for comparing the estimated efficacy to a physiological condition-specific threshold value wherein the efficacy threshold value is statistically determined using a patient population; and
   means for altering a delivery regimen of the currently configured ATP therapy when the estimated efficacy of the ATP therapy is deemed insufficient.

* * * * *

UNITED STATES PATENT AND TRADEMARK OFFICE
CERTIFICATE OF CORRECTION

PATENT NO.        : 7,873,414 B2                                     Page 1 of 1
APPLICATION NO.   : 11/736286
DATED             : January 18, 2011
INVENTOR(S)       : Yanting Dong et al.

It is certified that error appears in the above-identified patent and that said Letters Patent is hereby corrected as shown below:

In column 12, line 8, in Claim 1, after "therapy" insert -- ; --.

In column 13, line 21, in Claim 10, delete "previous." and insert -- previous tachyarrhythmia episodes. --, therefor.

In column 15, line 23, in Claim 32, after "wherein" delete "the".

In column 16, line 23, in Claim 37, after "value" insert -- , --.

Signed and Sealed this
Fifth Day of April, 2011

David J. Kappos
*Director of the United States Patent and Trademark Office*